(12) United States Patent
Bruna

(10) Patent No.: US 7,137,391 B2
(45) Date of Patent: Nov. 21, 2006

(54) DOSIMETER FOR FLUID PRODUCT DISPENSER

(75) Inventor: Pascal Bruna, Sotteville les Rouen (FR)

(73) Assignee: Valois S.A.S., Le Neubourg (FR)

( * ) Notice: Subject to any disclaimer, the term of this patent is extended or adjusted under 35 U.S.C. 154(b) by 117 days.

(21) Appl. No.: 10/491,567

(22) PCT Filed: Oct. 3, 2002

(86) PCT No.: PCT/FR02/03376

§ 371 (c)(1),
(2), (4) Date: Apr. 5, 2004

(87) PCT Pub. No.: WO03/028792

PCT Pub. Date: Apr. 10, 2003

(65) Prior Publication Data

US 2004/0255935 A1    Dec. 23, 2004

(30) Foreign Application Priority Data

Oct. 4, 2001    (FR)    ................................. 01 12771

(51) Int. Cl.
*A62B 7/00*    (2006.01)
(52) U.S. Cl. .............................. 128/205.23; 128/200.11

(58) Field of Classification Search ........... 128/200.11, 128/200.12, 200.14, 200.17, 200.18, 200.23, 128/202.22, 203.12, 203.15, 203.21, 205.23; 116/308

See application file for complete search history.

(56) References Cited

U.S. PATENT DOCUMENTS 3,495,567 A * 2/1970 Hayes et al. ................ 116/308
3,713,582 A   1/1973 Furuoka

FOREIGN PATENT DOCUMENTS

| EP | 0 684 047 A | 11/1995 |
| EP | 0 949 584 A | 10/1999 |
| FR |   637 259 A |  4/1928 |
| FR | 2 799 858 A |  4/2001 |
| WO | WO 98 52634 A | 11/1998 |
| WO | WO 01 37909 A |  5/2001 |

* cited by examiner

Primary Examiner—Henry Bennett
(74) Attorney, Agent, or Firm—Sughrue Mion, PLLC

(57) ABSTRACT

A fluid-dispenser dose counter including two superposed count disks (10, 20). The first disk (10) may be a units disk, and the second disk (20) may be a tens and/or hundreds disk. Each disk (10, 20) is rotatably mounted about an axis of rotation (23, 33), the axes of rotation (23, 33) being parallel to and offset from each other. The counter also includes a cover (30). The cover (30) may define the axis of rotation (33) of the first disk (10) and the axis of rotation (23) of the second disk (20).

20 Claims, 4 Drawing Sheets

1

DOSIMETER FOR FLUID PRODUCT DISPENSER

The present invention relates to a fluid-dispenser dose counter, and to a fluid dispenser incorporating such a counter.

In the field of fluid dispensers, and in particular in the field of pharmacy, it is known to use a dose counter for determining the number of doses that have been dispensed or that remain to be dispensed in the dispenser. Such counters are generally actuated when the dispenser is used, in such a manner that they are designed to count each time a dose of fluid is expelled by the dispenser. The presence of a dose counter in a fluid dispenser, whether it be a pump dispenser or a measuring-valve dispenser, implies a relatively significant structural modification to the dispenser in order to enable the counter to be fitted thereto. This results in manufacture and assembly that are more complicated, and therefore in an increase in the cost of the appliance in question. Another problem that is posed with existing counters is the difficulty in being able to count a high number of doses, which generally implies a fairly significant increase in the size of the counter, which may make it more complicated or even impossible to fit to a fluid dispenser. In addition, since fluid dispensers can be very different from one another, in particular depending on the type of dispenser used, namely a measuring valve or a pump, it is often difficult to fit the same counter to the various devices, such that it is often necessary to manufacture a new counter that is specific to each dispenser, thereby considerably increasing the cost of development and manufacture of the device.

An object of the present invention is to provide a fluid-dispenser dose counter which does not have the above-mentioned drawbacks.

A particular object of the present invention is to provide a dose counter which is simple and inexpensive to manufacture and to assemble.

Another object of the present invention is to provide a dose counter which is compact and small while enabling a large number of doses to be counted.

Another object of the present invention is to provide a dose counter which can be fitted very easily to all known types of fluid dispenser device.

Another object of the present invention is to provide a dose counter which is reliable, ergonomic, and easy to see for the user of the fluid dispenser on which the counter is mounted.

The present invention therefore provides a fluid-dispenser dose counter comprising two superposed count disks, a first disk that is a units disk, and a second disk that is a tens and/or hundreds disk, each disk being rotably mounted about an axis of rotation, said axes of rotation being parallel to and offset from each other, the counter being characterized in that it further comprises a cover, said cover defining the axis of rotation of the first disk and the axis of rotation of the second disk.

Advantageously, the tens and/or hundreds, second disk is transparent at least in part, and overlies the units, first disk in the observation direction of the user.

The cover advantageously overlies the count disks in the observation direction of the user, said cover incorporating a peripheral housing receiving the tens and/or hundreds, second disk, and being provided with a viewing window for the user, the axis of rotation of the first disk being offset relative to the axis of the cover which defines the axis of rotation of the second disk.

2

The first and second count disks advantageously include respective anti-return means allowing rotation to take place in the counting direction only.

The anti-return means of the units, first disk are advantageously formed by a radially-extending catch of the cover co-operating with peripheral radially-extending teeth of said first disk.

The anti-return means of the tens and/or hundreds, second disk are advantageously formed by an axially-extending projection inside the cover co-operating with peripheral axially-extending recesses in said second disk.

Preferably, the first disk is turned each time the fluid dispenser is actuated, and the second disk is turned by the first disk each time said first disk has performed one complete revolution.

Advantageously, the counter is a down-counter and counts the number of doses remaining in the fluid dispenser.

End-of-counting indicator means are advantageously provided.

In particular, said indicator means are provided on the tens and/or hundreds, second disk, and are made in the form of a portion that is partially and/or completely opaque.

The present invention also provides a fluid dispenser including a counter as defined above.

The dispenser preferably includes an actuator element designed to actuate the first count disk each time said dispenser is actuated.

Other characteristics and advantages of the present invention appear more clearly from the following detailed description of an embodiment thereof, made in relation to the accompanying drawings, and given by way of non-limiting example, in which.

Figure 2:
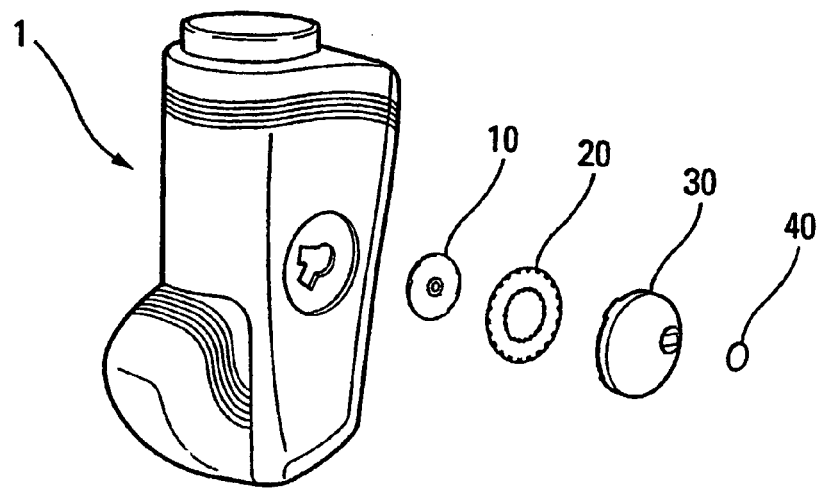
FIG. 2 is a partially-exploded diagrammatic view of a fluid dispenser incorporating a counter constituting an embodiment of the present invention.
Figure 3:
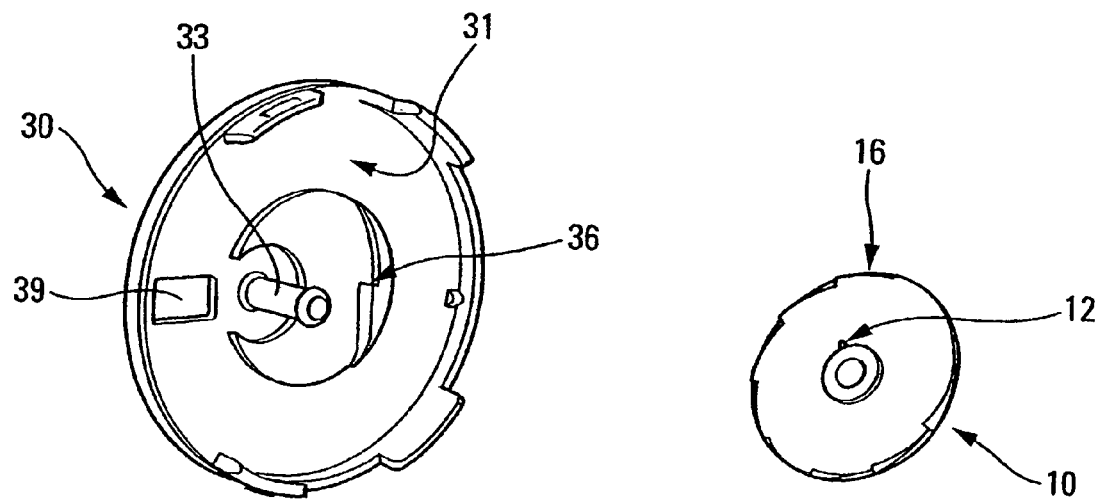
FIG. 3 is a diagrammatic perspective view showing the co-operation between the cover and the units, first disk of the counter of FIG. 1.

The embodiment shown in the drawings is a counter which applies more particularly to a device known as a "Measured-Dose Inhaler" as shown in FIG. 2. Naturally, however, the present invention is not limited to this type of dispenser device, and, on the contrary, it applies to all types of fluid dispenser as long as said fluid dispensers include an element that moves during actuation and enables the counter to be actuated. For example, any dispenser comprising a reservoir and a pump mounted on the reservoir can receive a counter as described in the present invention, and the actuator element which co-operates with the counter can be any part that is displaced during actuation, e.g. the dispenser head, the pusher, the reservoir, or an element that is secured thereto, etc. In the example shown in FIG. 2, the element which actuates the counter is an actuator element 5 (not shown in FIG. 2) which is generally secured to the reservoir, said actuator element being pressed into the body of the device to dispense a dose of fluid.

The counter is described below in more general manner, with reference to the figures, and without being specifically directed to the Measured Dose Inhaler dispenser shown in FIG. 2. Said dispenser is, however, an illustrative example, and it shows, in particular, that the counter can be used in vertical manner in a side wall of the device. This is likewise one possible embodiment configuration amongst others, and the counter of the invention can equally well be used in a different position to that of FIG. 2.

The fluid-dispenser dose counter comprises two count disks 10 and 20 which are axially superposed one on the other. The first count disk 10 is the units disk, and consequently it is designed to perform one complete revolution made up of ten partial turns through 36°. The second count disk is the tens and/or hundreds disk 20. A characteristic of the counter of the invention is that the two count disks turn about axes of rotation which are parallel but offset from each other. This makes it possible, in particular, for the units disk 10 to be substantially smaller than the tens and/or hundreds disk 20, while providing good visibility for the number of doses counted.

In the invention, the counter includes a cover 30 which defines both the axis of rotation 33 of the first disk 10 and the axis of rotation 23 of the second disk.

Preferably, the tens and/or hundreds, second disk 20 is transparent at least in part, and overlies the units, first disk 10 in the observation direction of the user. In this way, the units figure shows through, as can be seen clearly in FIG. 9 which shows the counted number, namely number 115, which appears in a viewing window 39 of the counter.

The cover 30 advantageously incorporates the viewing window 39. The cover 30 is designed to receive the tens and/or hundreds, second disk 20 in a housing 31 provided for this purpose, said second disk 20 turning about the central axis of said cover which therefore forms the axis of rotation 23 of said second disk 20. As explained above, the cover 30 also defines the axis 33 which is in the form of a pin on which the first count disk 10 is assembled, said axis 33 being offset from the axis 23 of the second disk. This offset appears particularly clearly in the figures. Advantageously, it is the first disk 10, once mounted on the pin 33 that holds the second disk 20 in place in the housing 31.

Advantageously, the counter includes anti-return means for the first count disk 10 and for the second count disk 20. In the example shown in the figures, the anti-return means are preferably formed on the cover 30. Thus, the first anti-return means for the units, first disk 10 are advantageously formed by a radially-extending catch 36 of the cover which co-operates with peripheral radially-extending teeth 16 of said first disk 10. The second anti-return means of the tens and/or hundreds, second disk 20 are advantageously formed by an axially-extending projection 35 inside the cover 30 which co-operates with corresponding peripheral axially-extending recesses 25 in said second disk 20. In this variant, the second anti-return means therefore do not really prevent the second disk 20 from turning in the opposite direction to that which is imparted thereto during actuation of the counter, but they prevent any accidental displacement of the second disk 20, during storage or transport, or during any use other than that of dispensing a dose of fluid via the dispenser. The axially-extending projection 35 of the cover penetrates into a respective recess of the disk 20, and a certain force is required to disengage said axially-extending projection 35 from said axially-extending recess 25, thus enabling the second disk 20 to turn, said axially-extending projection 35 then coming into co-operation with the following axially-extending recess 25 on the periphery of the disk 20.

Figure 1:
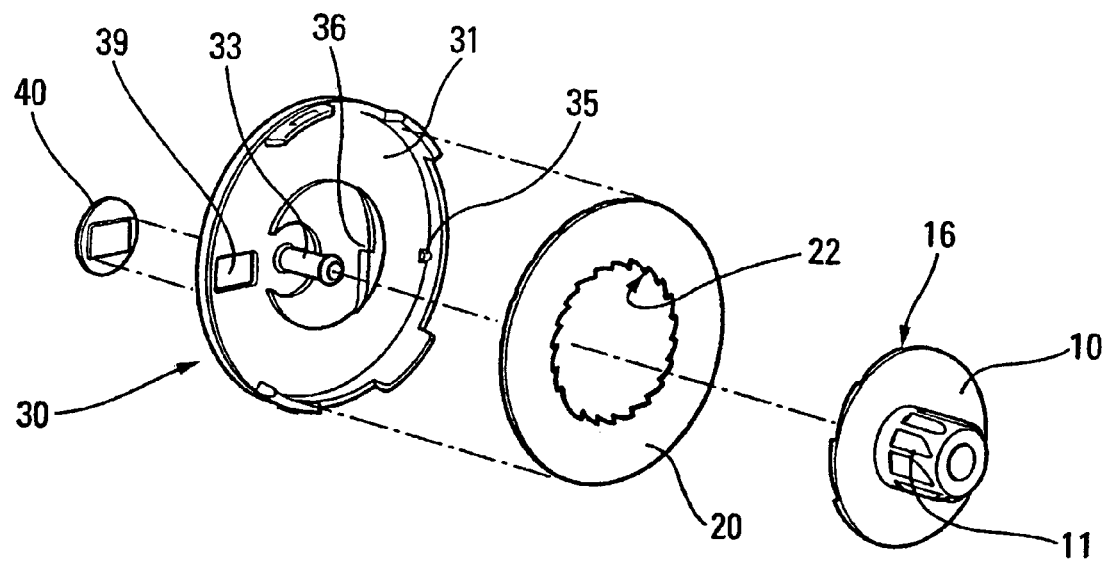
FIG. 1 is an exploded diagrammatic view of a counter constituting an embodiment of the present invention.
Figure 5:
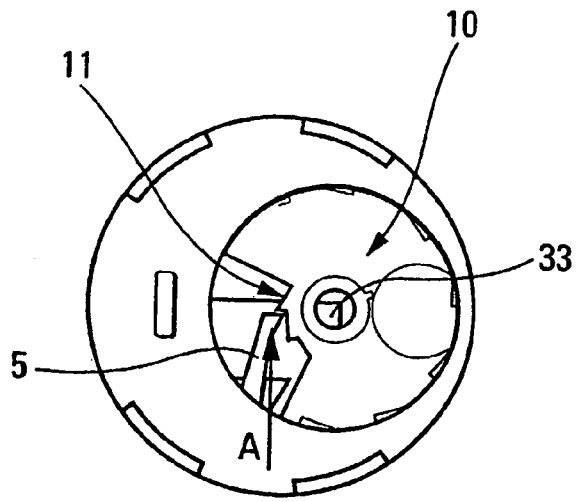
FIGS. 5 to 8 show an actuating sequence for the units, first disk.
Figure 6:
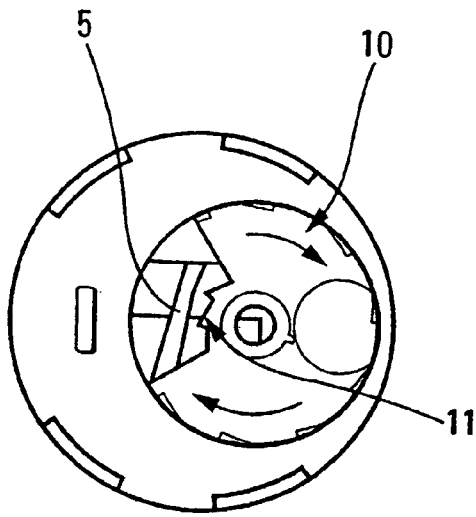
Figure 7:
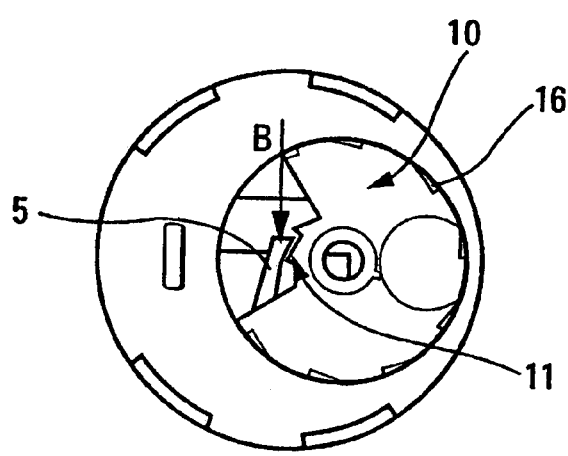
Figure 8:
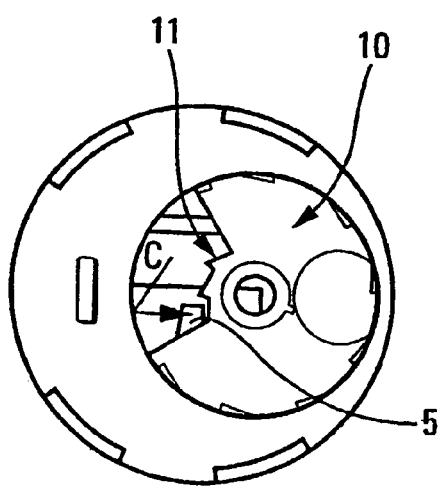

FIGS. 5 to 8 show an actuation cycle for actuating the units, first disk 10 by means of an actuator element 5 secured to the fluid dispenser. FIGS. 5 to 8 are partially cut away to enable said actuator element 5 to be seen. The units, first disk 10 includes a series of ten peripheral teeth 11, shown more clearly in FIG. 1. When the user actuates the device, the actuator element 5 comes into co-operation with a tooth 11, and, by moving in the direction of arrow A in FIG. 5, causes said first disk 10 to turn about its axis of rotation 33. FIG. 5 shows the end of actuation of the actuator element 5, with the disk 10 having turned through an angle of 36° corresponding to counting one unit. When the fluid dispenser returns to its rest position, the actuator element 5 also returns to its initial position, as shown by arrow B in FIG. 7. The actuator element 5 then slides over said teeth 11, and the units, first disk 10 is prevented from turning in the opposite direction by the first anti-return means formed in this case by the radially-extending teeth 16 of the units, first disk 10 co-operating with the radially-extending catch 36 of the cover (not shown in the figures). At the end of the cycle, the actuator element 5 snaps under the next tooth of the first disk, as shown by arrow C in FIG. 8. The device is then ready for a subsequent actuation cycle.

Each time the units, first disk 10 has performed one complete revolution, the second disk 20 is turned. The angle through which it is turned depends on the number of doses to be counted by means of the second disk 20. In the example shown in the figures, in particular FIGS. 9 to 11, the second count disk includes twenty counting positions, thereby enabling two hundred doses to be counted. Naturally, any number of doses can be counted by means of the counter of the present invention by modifying the numbers marked on the second disk 20. In order to cause the second count disk 20 to turn each time the units, first disk 10 has performed one complete revolution, said first disk includes a drive tooth 12 which comes into co-operation with teeth 22 of the second disk 20. In particular, the drive tooth 12 comes into contact with the teeth 22 of the second count disk 20 only once every complete revolution as a result of the offset between the axes of rotation of the two disks 10 and 20. In a variant, it is possible to provide a cam surface or any other similar means which enable the two disks to engage on each complete revolution of the first disk 10.

Figure 4:
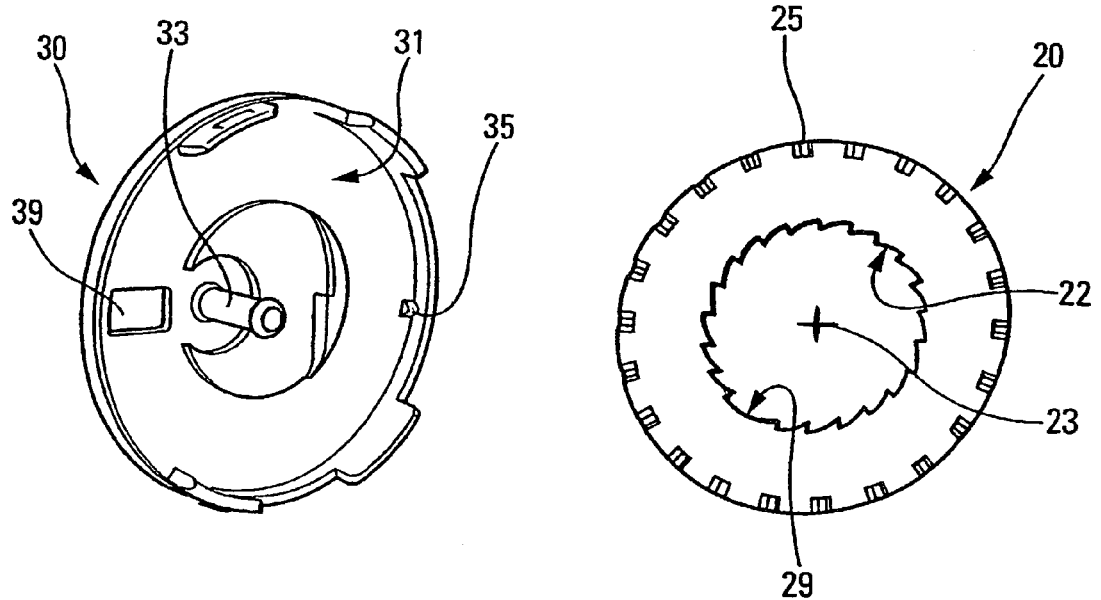
FIG. 4 is a view similar to that of FIG. 3, showing the co-operation between the cover and the tens and/or hundreds, second disk.
Figure 9:
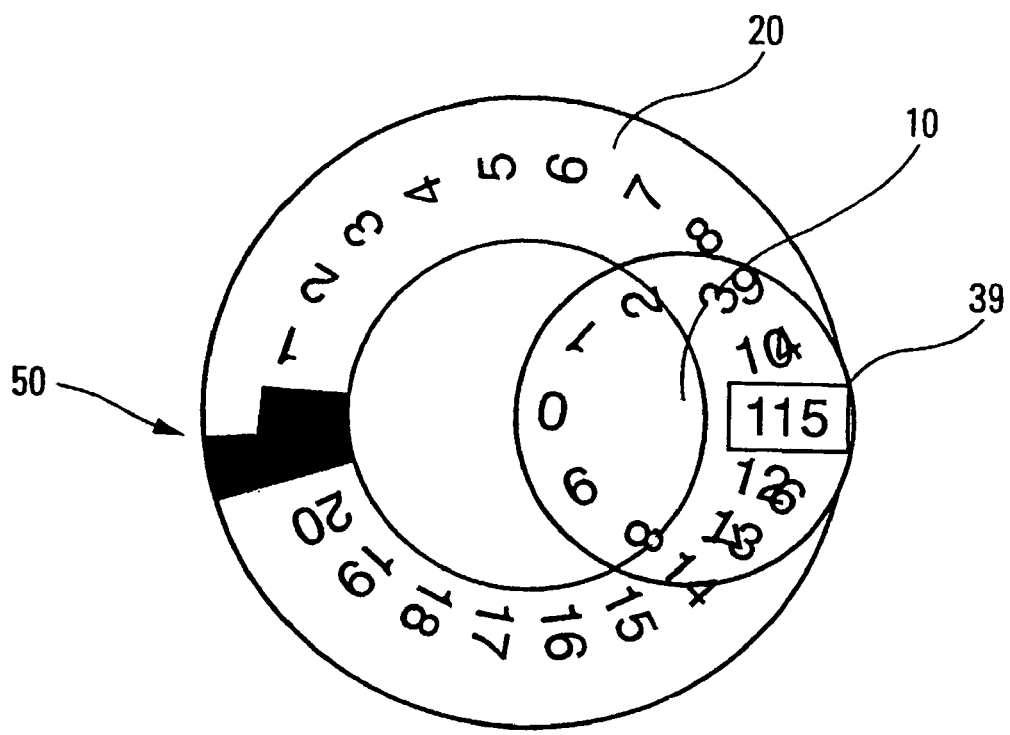
FIG. 9 is a diagrammatic plan view of the counter in an embodiment of the present invention.
Figure 10:
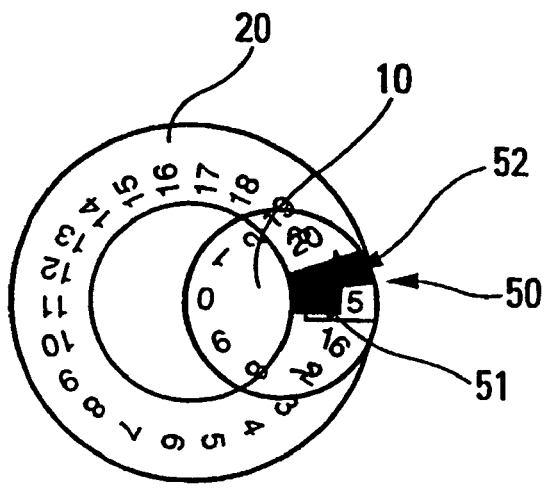
FIGS. 10 and 11 are views similar to that of FIG. 9 showing the operation of-the end-of-counting indicator means.
Figure 11:
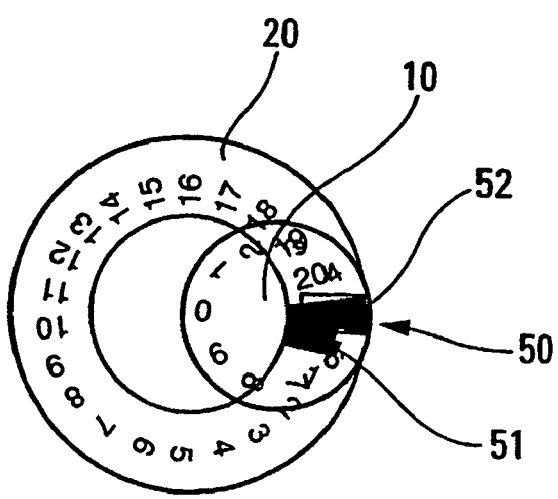

Preferably, the counter also includes end-of-counting indicator means 50. These are shown in FIGS. 10 and 11. Thus, in the embodiment shown in these drawings, the counter is a down-counter and is designed to count the number of doses that remain in the device, i.e. the number of doses decreases on each actuation. The end-of-counting indicator means 50 thus advantageously include a first portion 51 and a second portion 52. The first portion 51 of the indicator means 50 is designed so as to allow only numbers marked on the units, first count disk 10 to be seen, so that when only ten doses remain, the user is warned by the presence of said first portion 51 of the indicator means 50 in the viewing window 39. When the last dose has been dispensed, the second portion 52 of the indicator means 50 comes to obscure the viewing window 39 completely, and the user then knows that there are no longer any doses to be dispensed, or that the originally-intended number of doses has been dispensed. The indicator means 50 are advantageously made by partially and/or completely opaque portions of the second count disk 20, as can be seen in FIGS. 9 to 11. In order to prevent subsequent actuations from turning the second disk, thereby freeing the viewing window 39, provision can be made, at the end-of-counting indicator means, in particular at the second portion 52 which completely obscures the window 39, to ensure there is no possibility of the two count disks 10 and 20 co-operating. By way of example, this can be achieved by omitting one tooth 22, as shown at 29 in FIG. 4. In this case, even if the units, first disk 10 goes through another complete revolution during subsequent actuations of the device, the second disk 20 no longer turns and the window 39 remains obscured. The rotation of the units, first disk 10 is not a problem since the numbers cannot be seen by the user because they are obscured by the end-of-counting indicator means 50 of the second disk 20, which overlie the numbers in the observation direction.

Advantageously, the counter further includes a magnifying lens 40 disposed on the viewing window 39 so as to enable the number marked in said window to be magnified, and so as to make it easier for the user to see the number of doses counted or remaining in the device, depending on the type of counter.

Although the invention has been described with reference to a particular embodiment thereof, it is in no way limited to that embodiment. On the contrary, the person skilled in the art can apply any desired modifications thereto without going beyond the ambit of the present invention as defined by the accompanying claims.

The invention claimed is:

1. A fluid-dispenser dose counter comprising:
a first count disk (10);
a second count disk (20) superposed with said first disk; and
a cover;
wherein each disk (10, 20) is rotatably mounted about a separate axis of rotation (23, 33), said axes of rotation (23, 33) being parallel to and offset from each other.

2. A counter according to claim 1, wherein the second disk (20) is at least partially transparent and overlies the first disk (10) in an observation direction of the user.

3. A counter according to claim 1, wherein the cover (30) overlies the count disks (10, 20) in the observation direction of the user, said cover (30) comprises a peripheral housing (31) that receives the second disk (20), and said cover further comprises a viewing window (39); and
wherein the axis of the cover (30) defines the axis of rotation (23) of the second disk (20).

4. A counter according to claim 1, in which the first and second count disks (10, 20) include respective anti-return means (16, 36; 25, 35) allowing rotation to take place in a counting direction only.

5. A counter according to claim 4, in which the anti-return means (16, 36) of the first disk (10) is formed by a radially-extending catch (36) of the cover (30) co-operating with peripheral radially-extending teeth (16) of said first disk (10).

6. A counter according to claim 4, in which the anti-return means (25, 35) of the second disk (20) is formed by an axially-extending projection (35) inside the cover (30) co-operating with peripheral axially-extending recesses (25) in said second disk (20).

7. A fluid dispenser (1), characterized in that said fluid dispenser includes a counter according to claim 1.

8. A fluid dispenser according to claim 7, in which the first disk (10) is turned each time the fluid dispenser is actuated, and the second disk (20) is turned by the first disk (10) each time said first disk has performed one complete revolution.

9. A fluid dispenser according to claim 7, in which the counter is a down-counter and counts the number of doses remaining in the fluid dispenser.

10. A counter according to claim 1, in which end-of-counting indicator means (50) is provided.

11. A counter according to claim 10, in which said indicator means (50) is provided on the second disk (20), and are made in the form of a portion that is partially and/or completely opaque (51, 52).

12. A dispenser according to claim 7, including an actuator element (5) designed to actuate the first count disk (10) each time said dispenser (1) is actuated.

13. A counter according to claim 1 wherein said second disk displays at least one of a tens and a hundreds place and said first disk displays a units place.

14. A counter according to claim 1 wherein the cover defines the axis of rotation of the first disk and the axis of rotation of the second disk.

15. A counter according to claim 1, further comprising a radially-extending catch formed on one of said first disk and said cover and radially-extending teeth formed on the other of said first disk and said cover;
wherein, said radially-extending catch and said radially-extending teeth cooperate to limit said first disk to rotate in only one direction.

16. A counter according to claim 1, further comprising an axially-extending projection formed on one of said second disk and said cover and axially-extending recesses formed on the other of said second disk and said cover;
wherein said axially-extending projection and said axially-extending recesses cooperate to prevent rotation of the second disk when said counter is not being actuated.

17. A counter according to claim 1, wherein at least one of said first disk and said second disk includes an indicator and wherein at least a portion of said indicator is displayed to indicate the end of at least one of said disks.

18. A counter according to claim 17, wherein said indicator comprises a first portion and a second portion and said first portion of said indicator extends longer in the radial direction than said second portion of said indicator such that a second portion of said indicator is displayed to indicate the end of the second disk and the first portion of said indicator is displayed to indicate the end of both the first and the second disks.

19. A counter according to claim 17 wherein said indicator is at least partially opaque.

20. A counter according to claim 1, further comprising an actuator element (5) designed to actuate rotate said count disks and wherein once said second disk has completed a revolution, said actuator can no longer rotate said second count disk.

* * * * *